United States Patent
Receveur et al.

(10) Patent No.: US 8,569,633 B2
(45) Date of Patent: Oct. 29, 2013

(54) FEEDTHROUGH FOR MICROELECTROMECHANICAL SYSTEM

(75) Inventors: Rogier Receveur, Maastricht (NL);
Michael A. Schugt, St. Paul, MN (US);
William J. Taylor, Anoka, MN (US);
Brad C. Tischendorf, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 865 days.

(21) Appl. No.: 11/949,005

(22) Filed: Nov. 30, 2007

(65) Prior Publication Data
US 2008/0283293 A1    Nov. 20, 2008

Related U.S. Application Data

(60) Provisional application No. 60/868,007, filed on Nov. 30, 2006.

(51) Int. Cl.
*H05K 7/00* (2006.01)
(52) U.S. Cl.
USPC ............ 174/650; 361/782; 361/783; 361/784
(58) Field of Classification Search
USPC .................................. 174/650; 361/782–784
See application file for complete search history.

(56) References Cited

U.S. PATENT DOCUMENTS

| | | | |
|---|---|---|---|
| 4,935,583 A * | 6/1990 | Kyle | 174/152 GM |
| 5,104,755 A * | 4/1992 | Taylor et al. | 429/181 |
| 5,821,011 A * | 10/1998 | Taylor et al. | 429/181 |
| 6,433,276 B1 * | 8/2002 | Bellora | 174/50.61 |
| 6,516,808 B2 * | 2/2003 | Schulman | 128/899 |
| 6,536,882 B1 | 3/2003 | Hawkins et al. | |
| 6,603,182 B1 | 8/2003 | Low et al. | |
| 6,759,309 B2 | 7/2004 | Gross | |
| 6,888,233 B2 | 5/2005 | Horning et al. | |
| 6,924,165 B2 | 8/2005 | Horning et al. | |
| 7,098,117 B2 * | 8/2006 | Najafi et al. | 438/456 |
| 7,190,051 B2 * | 3/2007 | Mech et al. | 257/632 |
| 7,837,085 B1 * | 11/2010 | Tziviskos | 228/122.1 |
| 2004/0126953 A1 | 7/2004 | Cheung | |
| 2004/0152229 A1 | 8/2004 | Najafi et al. | |
| 2004/0180464 A1 | 9/2004 | Horning et al. | |
| 2004/0244484 A1 | 12/2004 | Horning et al. | |
| 2006/0192272 A1 | 8/2006 | Receveur | |

* cited by examiner

*Primary Examiner* — William H Mayo, III
*Assistant Examiner* — Hiram E Gonzalez
(74) *Attorney, Agent, or Firm* — Evans M. Mburu

(57) ABSTRACT

A hermetically sealed microelectromechanical system (MEMS) package for an implantable medical device is presented. The MEMS comprises a first substrate that includes an aperture. A feedthrough assembly is coupled to the aperture, the feedthrough assembly comprises a conductive element housed in a glass insulator member. A second substrate is coupled to the first substrate.

26 Claims, 2 Drawing Sheets

FEEDTHROUGH FOR MICROELECTROMECHANICAL SYSTEM

RELATED APPLICATIONS

The present application claims priority and other benefits from U.S. Provisional Patent Application Ser. No. 60/868,007 filed Nov. 30, 2006, incorporated herein by reference in its entirety.

FIELD OF THE INVENTION

The present invention relates generally to an implantable medical device (IMD) and, more particularly, to formation of a feedthrough assembly in a microelectromechanical system.

BACKGROUND

Numerous devices (e.g., implantable medical devices (IMDs), electrochemical cells (e.g. batteries, capacitors etc.), sensors etc.) are hermetically sealed to prevent liquid from contacting electronic components within the device. A typical feedthrough assembly consists of a conductive element (e.g., wires etc.), a ferrule, an insulator member (e.g. glass, ceramic etc.), and a seal. The ferrule includes an aperture configured to receive the insulator member. A seal is located between the ferrule and the insulator member. An exemplary feedthrough assembly may be inserted, for example, into a housing of a battery such that a portion of the conductive element extends into the housing to connect with battery elements while another portion of the conductive element extends outside of the housing to connect with other electronic components. It is desirable to develop new feedthroughs for IMDs.

DETAILED DESCRIPTION

One embodiment of the invention involves a feedthrough assembly in a microelectromechanical system (MEMS) package. The conductive hermetic feedthrough connects an interior cavity in the MEMS device to another electrononic component or device (e.g. lead interconnect etc.) outside of the MEMs package. The MEMS package is hermetic and isolated from body fluid contact more so than packages that employ an epoxy attachment to a silicon substrate.

Figure 1:
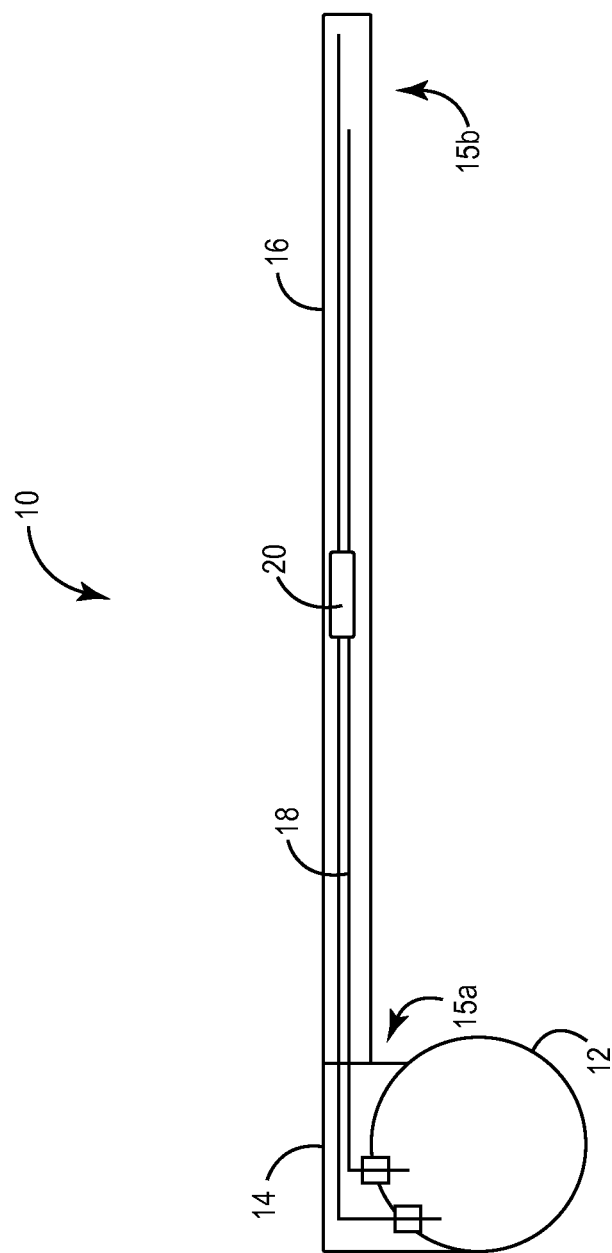
FIG. 1 depicts a schematic view of an implantable medical device.

FIG. 1 depicts a functional unit 20 in a medical device system 10. Functional unit 20 includes a feedthrough assembly (not shown) on or in an integrated circuit (IC), a substrate that includes electronic components (e.g. transistors, logic gates, switches etc.), or a substrate alone. Functional unit 20 can be used anywhere outside the medical device 12 and is electrically connected to one or more conductor(s) 18. For example, functional unit 20 serves as a sensor (e.g. pressure sensor etc.) that employs a feedthrough assembly.

Medical device system 10 includes a medical device housing 12 having a connector module 14 that electrically couples various internal electrical components of medical device housing 12 to a proximal end 15a of a medical lead 16 such as one or more conductors 18 (e.g. coil, wire etc.) that extend to a distal end 15b of lead 16. Medical device system 10 may comprise any of a wide variety of medical devices that include one or more medical lead(s) 16 and circuitry coupled to the medical lead(s) 16. By way of example, medical device system 10 may take the form of an implantable cardiac pacemaker that provides therapeutic stimulation to the heart or a neurostimulator. Alternatively, medical device system 10 may take the form of an implantable cardioverter, an implantable defibrillator, an implantable cardiac pacemaker-cardioverter-defibrillator (PCD), an implantable pulse generator, or an implantable medical device that solely monitors conditions associated with the patient.

Figure 2:
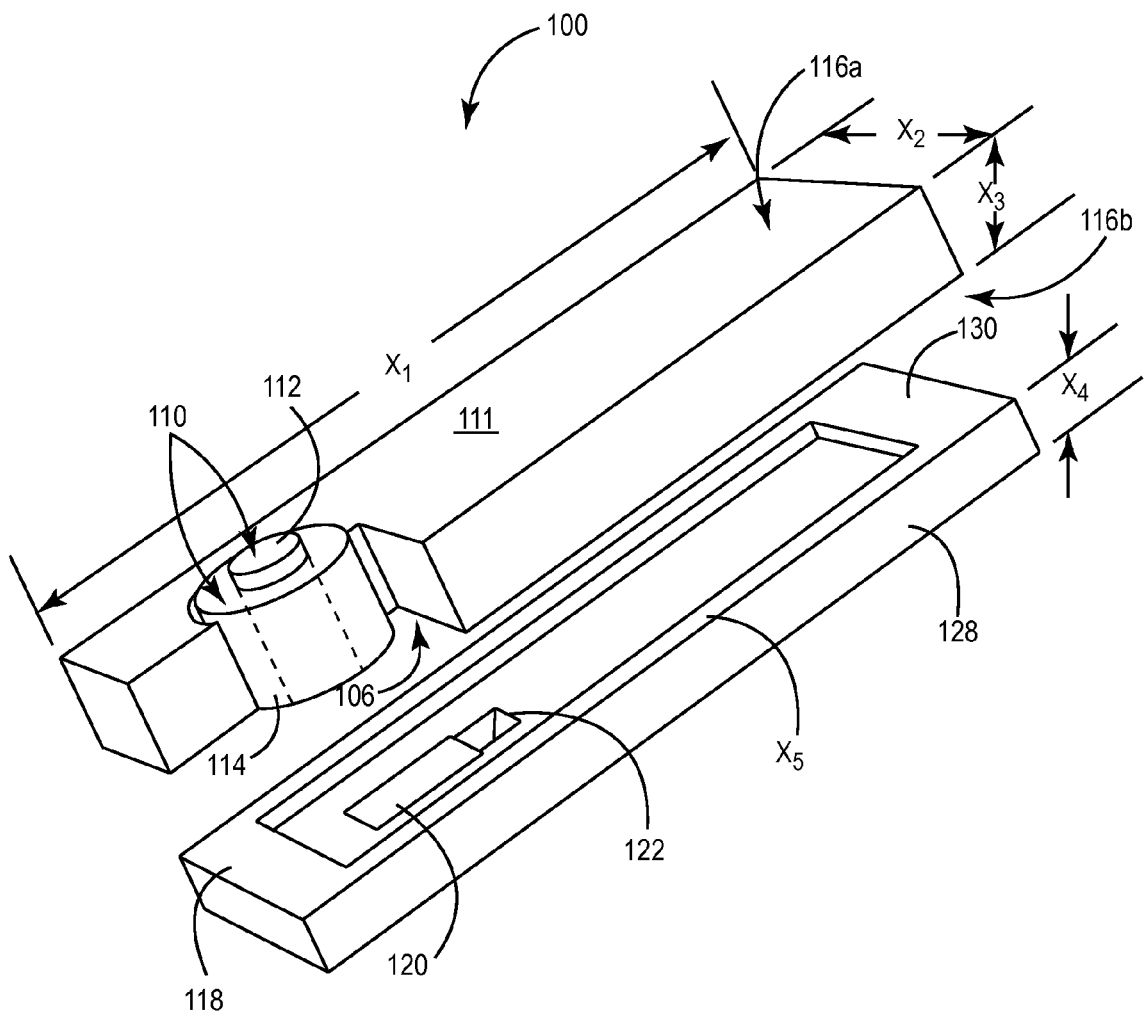
FIG. 2 is a schematic cut away view of a MEMS package that includes a feedthrough assembly.

FIG. 2 illustrates one embodiment of a MEMS package 100 for medical device system 10. MEMS package 100, in one embodiment, is used in or for a sensor. For example, a MEMS package 100 could be associated with a transducer, which converts a signal into an electrical signal (i.e. voltage, current etc.).

MEMS package 100 includes a feedthrough assembly 110, a first substrate 111, and a second substrate 128. Feedthrough assembly 110 is hermetically disposed in an aperture 106 of first substrate 111, and coupled to second substrate 128. Feedthrough assembly 110 (e.g. glass-pin-insulator seal) comprises a conductive element 112 (i.e. pin) hermetically housed in an insulator member 114 (also referred to as sealing glass). Conductive element 112 is formed of a conductive material such as tantalum (Ta), niobium (Nb), titanium (Ti), platinum (Pt), iridium (Ir) and/or alloys thereof.

Insulator member 114 is formed of glass. Typical glass for formation of insulator member 114 comprises boro-alumino, boro-alumino silicate and/or boro silicate type glasses with a wide range of thermal expansions to approximately match biostable conductive element 112 materials such as Ta, Nb, niobium-titanium (Nb—Ti) alloy, Pt, Pt alloys, Ti, alloys of Ti and/or other suitable materials. The element(s) and/or compounds used to form insulator member 114 are selected in a manner to reduce tensile stresses with conductive element 112. For example, insulator member 114, employing glass, has a CTE value about equivalent to or within 15% of the CTE associated with conductive element 110.

Conductive element 112 and first substrate 111 are hermetically joined by the insulator material (e.g. glass etc.) of insulator member 114 melting and engaging conductive element 112 and the inner walls of aperture 106. The hermetic seal could be a CTE match, or an approximate match (i.e. CTE within 10%) for all MEMS package components. In another embodiment, the CTE within 5%) for all MEMS package components. In another embodiment, the CTE within 2.5%) for all MEMS package components. In yet another embodiment, first substrate 111 (i.e. housing) possesses a CTE greater than insulator member 114 and conductor 112, thereby forming a compression seal.

First substrate 111 includes a first surface 116a (also referred to as ceramic or glass housing material), a second surface 116b (i.e. silicon material), length X1, width X2, thickness X3, and an aperture 106 for receiving feedthrough assembly 110. First substrate 111 contains the hermetic seal feedthrough assembly 110 and metallized tracings for establishing an electrical connection to second substrate 128. In one embodiment, first substrate 111 comprises a ceramic or glass having a coefficient thermal expansion (CTE) value equivalent to or greater than feedthrough 110 (i.e. pin/glass assembly).

In one embodiment, first substrate 111 is comprised of a material that has about an equivalent or greater CTE value then conductive element 112 and glass insulator member 114. First substrate 111 can include a ceramic such as for example, polycrystalline alumina with a CTE of about 8.0, sapphire (e.g. single crystal alumina, etc.) with a CTE of about 8.0, and zirconia with a CTE of about 10. In another embodiment, first substrate 111 or housing is made of glass instead of a ceramic, and possesses general characteristics such that (1) the glass has a higher melting point than insulator member 114; and/or (2) the glass has about an equivalent or greater CTE value than the sealing glass.

Second substrate 128 includes via 122, a metallized trace 120 and includes electronic components that allow MEMS package 110 to function as a sensor substrate such as a transducer; however, skilled artisans appreciate that the substrate may be configured to include any type of circuitry such as switches, signal processing capability, and/or any other suitable form of circuitry related to an implantable medical devices. Second substrate 128 possesses about the same or similar dimensions as first substrate 111. For example, thickness X4 is the same or about the same as X3. Wall thickness X5 forms a perimeter on the first surface 130 of second substrate 128. The second surface (not shown) of second substrate 128 is typically directly adjacent to the housing of an implantable medical device.

Feedthrough assembly 110, disposed in first substrate 111, is then coupled through joint 118 (e.g. a frit joint etc.) to second substrate 128 (also referred to as a silicon MEMS substrate). Coupling of first substrate 111 to the second substrate 128 is achieved by use of a glass frit, an Au-silicon eutectic material or other suitable material 118. Second substrate 128 (silicon) material generally has a higher melting point than the glass used to create to a glass insulator member 114. Conductive element 110 is electrically connected to second substrate 128 through a metal tracing 120. In one embodiment, the metal tracing 120 is located, for example, in second substrate 128.

Table 1, presented below, provides exemplary dimensions for components of MEMS package 100; however, skilled artisans appreciate that other dimensions may also be used.

TABLE 1

Exemplary dimensions for components of MEMS package

| Component | Dimension millimeters (mm) |
|---|---|
| Conductive element 112 diameter | 0.40 |
| Glass insulator member 114 diameter | 0.75 |
| length X1 | 3.50 |
| width X2 | 1.00 |
| thickness X3 | 0.40 |
| thickness X4 | 0.25 |
| Wall X5 | 0.25 |

Skilled artisans understand other embodiments may implement the principles described herein. For example, a functional unit 20 may be placed in a free body such as a lead. Additionally, while MEMS package is described relative to a sensor or a sensor component (i.e. transducer etc.), it is contemplated that MEMS package 100 can be used in a variety of ways to achieve certain functions of implantable medical devices.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A micro electromechanical system (MEMS) package for an implantable medical device comprising:

a first substrate that includes a first surface, a second surface, and an aperture extending through the first substrate from the first surface to the second surface;

a feedthrough assembly coupled to the aperture, the feedthrough assembly including a conductive element housed in a glass insulator member;

a second substrate comprising a first surface and a second surface, wherein the second substrate is coupled to the first substrate such that the first surface of the second substrate faces the second surface of the first substrate, further wherein the first substrate is coupled to the second substrate by joint material disposed on the first surface of the second substrate contacting the second surface of the first substrate, further wherein the first substrate is located adjacent the first surface of the second substrate but not the second surface of the second substrate such that the second surface of the second substrate is configured for positioning directly adjacent to a housing of an implantable medical device; and a metallized trace disposed on the first surface of the second substrate, wherein the conductive element is directly coupled to the metallized trace to electrically couple the conductive element to the second substrate.

2. A micro electromechanical system (MEMS) package for an implantable medical device comprising:

a first substrate that includes a first exterior surface, a second surface, and an aperture extending through the first substrate from the first exterior surface to the second surface;

a feedthrough assembly comprising a ceramic insulator and a conductive element housed in the ceramic insulator member, the feedthrough assembly disposed in the aperture;

a second substrate comprising a first surface and a second surface, wherein the second substrate is coupled to the first substrate such that the first surface of the second substrate faces the second surface of the first substrate, wherein the first substrate is located adjacent the first surface of the second substrate but not the second surface of the second substrate such that the second surface of the second substrate is configured for positioning directly adjacent to a housing of an implantable medical device, a metallized trace disposed on the first surface of the second substrate, wherein the conductive element is directly coupled to the metallized trace to electrically couple the conductive element to the second substrate; and wherein no conductive material exists between the conductive element and the first substrate.

3. The MEMS package of claim 2, wherein the ceramic insulator member comprises a material having a CTE similar to a CTE of the first substrate.

4. The MEMS package of claim 2, wherein the ceramic insulator member comprises a material having a CTE similar to a CTE of the second substrate.

5. The MEMS package of claim 2, wherein a metallized trace is disposed in a first surface of the second substrate.

6. The MEMS package of claim 2, wherein the conductive element includes at least one of Ta, Nb, Ti, Pt, Ir and alloys thereof.

7. A microelectromechanical system (MEMS) package for an implantable medical device comprising:

a first substrate that includes a first exterior surface, a second surface, and an aperture extending through the first substrate from the first exterior surface to the second surface;

a feedthrough assembly hermetically sealed in the aperture, the feedthrough assembly being exposed on an exterior surface of the first substrate, and wherein the feedthrough assembly includes:
 a glass insulator member sealed within the aperture; and
 a conductive pin extending through the insulator member;
a second substrate comprising a first surface and a second surface, wherein the second substrate is coupled to the first substrate such that the first surface of the second substrate faces the second surface of the first substrate, wherein the first substrate is located adjacent the first surface of the second substrate but not the second surface of the second substrate such that the second surface of the second substrate is configured for positioning directly adjacent to a housing of an implantable medical device;
a metallized trace disposed on the first surface of the second substrate, wherein the conductive element is directly coupled to the metallized trace to electrically couple the conductive element to the second substrate; and
wherein no conductive material exists between the conductive element and the first substrate.

8. The MEMS package of claim 7, wherein the glass insulator member comprises a material having a coefficient of thermal expansion (CTE) similar to a CTE of the first substrate.

9. The MEMS package of claim 8, wherein the glass insulator member comprises a material having a CTE within 2.5% of a CTE of the first substrate.

10. The MEMS package of claim 7, wherein the glass insulator member comprises a material having a CTE within 5% of a CTE of the first substrate.

11. The MEMS package of claim 7, wherein the glass insulator member comprises a material having a CTE within 10% of a CTE of the first substrate.

12. The MEMS package of claim 8, wherein the glass insulator member comprises a material having a CTE within 2.5% of a CTE of the second substrate.

13. The MEMS package of claim 7, wherein the glass insulator member comprises a material having a CTE within 5% of a CTE of the second substrate.

14. The MEMS package of claim 7, wherein the glass insulator member comprises a material having a CTE within 10% of a CTE of the second substrate.

15. The MEMS package of claim 7, wherein the conductive element includes at least one of tantalum (Ta), niobium (Nb), titanium (Ti), platinum (Pt), iridium (Ir) and alloys thereof.

16. The MEMS package of claim 7 wherein the glass insulator member comprises a material having a CTE similar to a CTE of the first substrate.

17. The MEMS package of claim 16, wherein the glass insulator member comprises a material having a CTE within 2.5% of a CTE of the first substrate.

18. The MEMS package of claim 16, wherein the glass insulator member comprises a material having a CTE within 5% of a CTE of the first substrate.

19. The MEMS package of claim 16, wherein the glass insulator member comprises a material having a CTE within 1% of a CTE of the first substrate.

20. The MEMS package of claim 7, wherein the second substrate includes a surface with a metalized trace disposed thereon, the metalized trace directly coupled to the conductive pin.

21. A MEMS package for an implantable medical device comprising:
a first substrate that includes a first exterior surface, a second surface, and an aperture extending through the first substrate from the first exterior surface to the second surface;
a feedthrough assembly hermetically sealed in the aperture comprising:
 a glass insulator member sealed within the aperture; and
 a conductive pin extending through glass insulator member;
a second substrate comprising a first surface and a second surface, wherein the second substrate is coupled to the first substrate such that the first surface of the second substrate faces the second surface of the first substrate, further wherein the first is coupled to the second substrate by joint material located between the second surface of the first substrate and the first surface of the second substrate, further wherein the first substrate is located adjacent the first surface of the second substrate but not the second surface of the second substrate such that the second surface of the second substrate is configured for positioning directly adjacent to a housing of an implantable medical device;
a metallized trace disposed on the first surface of the second substrate, wherein the conductive element is directly coupled to the metallized trace to electrically couple the conductive element to the second substrate; and
wherein no conductive material exists between the conductive element and the first substrate.

22. A microelectromechanical system (MEMS) package for an implantable medical device comprising:
a first substrate that includes a first exterior surface, a second surface, and an aperture extending through the first substrate from the first exterior surface to the second surface;
a feedthrough assembly hermetically sealed in the aperture comprising:
 a glass insulator member sealed within the aperture; and
 a conductive pin extending through glass insulator member;
a second substrate comprising a first surface and a second surface, wherein the second substrate is coupled to the first substrate by joint material located between the second surface of the first substrate and the first surface of the second substrate such that the first surface of the second substrate faces the second surface of the first substrate, wherein the first substrate is located adjacent the first surface of the second substrate but not the second surface of the second substrate such that the second surface of the second substrate is configured for positioning directly adjacent to a housing of an implantable medical device;
a metallized trace disposed on the first surface of the second substrate, wherein the conductive element is directly coupled to the metallized trace to electrically couple the conductive element to the second substrate; and
wherein no conductive material exists between the conductive element and the first substrate.

23. The MEMS package of claim 22, wherein the first substrate comprises one of polycrystalline alumina and single crystal alumina.

24. A microelectromechanical system (MEMS) package for an implantable medical device comprising:

a first substrate that includes a first exterior surface, a second surface, and an aperture extending through the first substrate from the first exterior surface to the second surface;

a feedthrough assembly hermetically sealed in the aperture, the feedthrough assembly being exposed on the second surface of the first substrate, and wherein the feedthrough assembly includes:

a glass insulator member sealed within the aperture; and a conductive pin extending through the insulator member;

a second substrate comprising a first surface and a second surface, wherein the second substrate is coupled to the first substrate such that the first surface of the second substrate faces the second surface of the first substrate, further wherein the first substrate is coupled to the second substrate by joint material located between the second surface of the first substrate and the first surface of the second substrate, further wherein the first substrate is located adjacent the first surface of the second substrate but not the second surface of the second substrate such that the second surface of the second substrate is configured for positioning directly adjacent to a housing of an implantable medical device;

a metallized trace disposed on the first surface of the second substrate, wherein the conductive element is directly coupled to the metallized trace to electrically couple the conductive element to the second substrate; and wherein no conductive ferrule exists between the conductive element and the first substrate.

25. A MEMS package for an implantable medical device comprising:

a first substrate that includes a first exterior surface, a second surface, and an aperture extending through the first substrate from the first exterior surface to the second surface;

a feedthrough assembly hermetically sealed in the aperture, the feedthrough assembly including a conductive element housed solely in a glass insulator member;

a second substrate comprising a first surface and a second surface, wherein the second substrate is coupled to the first substrate such that the first surface of the second substrate faces the second surface of the first substrate, further wherein the first substrate is coupled to the second substrate by joint material located between the second surface of the first substrate and the first surface of the second substrate, further wherein the first substrate is located adjacent the first surface of the second substrate but not the second surface of the second substrate such that the second surface of the second substrate is configured for positioning directly adjacent to a housing of an implantable medical device;

a metallized trace disposed on the first surface of the second substrate, wherein the conductive element is directly coupled to the metallized trace to electrically couple the conductive element to the second substrate;

wherein the first substrate comprises glass, and wherein no conductive material exists between the conductive element and the first substrate.

26. A MEMS package for an implantable medical device comprising:

a first substrate that includes a first exterior surface, a second surface, and an aperture extending through the first substrate from the first exterior surface to the second surface;

a feedthrough assembly hermetically sealed in the aperture, the feedthrough assembly including a conductive element housed solely in a glass insulator member; and a second substrate comprising a first surface and a second surface, wherein the second substrate is coupled to the first substrate such that the first surface of the second substrate faces the second surface of the first substrate, wherein the first substrate is located adjacent the first surface of the second substrate but not the second surface of the second substrate such that the second surface of the second substrate is configured for positioning directly adjacent to a housing of an implantable medical device;

a metallized trace disposed on the first surface of the second substrate, wherein the conductive element is directly coupled to the metallized trace to electrically couple the conductive element to the second substrate; and wherein the first substrate comprises glass, and wherein no conductive ferrule exists between the conductive element and the first substrate.

* * * * *